US010128079B2

(12) United States Patent
Walden, II et al.

(10) Patent No.: US 10,128,079 B2
(45) Date of Patent: Nov. 13, 2018

(54) MEMS FRAME HEATING PLATFORM FOR ELECTRON IMAGABLE FLUID RESERVOIRS OR LARGER CONDUCTIVE SAMPLES

(71) Applicant: PROTOCHIPS, INC., Morrisville, NC (US)

(72) Inventors: Franklin Stampley Walden, II, Raleigh, NC (US); John Damiano, Jr., Apex, NC (US); Daniel Stephen Gardiner, Wake Forest, NC (US); David P. Nackashi, Raleigh, NC (US); William Bradford Carpenter, Asheville, NC (US)

(73) Assignee: Protochips, Inc., Morrisville, NC (US)

( * ) Notice: Subject to any disclaimer, the term of this patent is extended or adjusted under 35 U.S.C. 154(b) by 129 days.

(21) Appl. No.: 15/253,126

(22) Filed: Aug. 31, 2016

(65) Prior Publication Data

US 2017/0062177 A1   Mar. 2, 2017

Related U.S. Application Data

(60) Provisional application No. 62/212,241, filed on Aug. 31, 2015.

(51) Int. Cl.
    *H01J 37/20*     (2006.01)
(52) U.S. Cl.
    CPC ....... *H01J 37/20* (2013.01); *H01J 2237/2001* (2013.01); *H01J 2237/2002* (2013.01); *H01J 2237/2003* (2013.01)

(58) Field of Classification Search
    USPC .......................... 250/440.11, 443.1
    See application file for complete search history.

(56) References Cited

U.S. PATENT DOCUMENTS

| 7,713,053 | B2 | 5/2010 | Mick et al. |
| 8,466,432 | B2 | 6/2013 | Damiano, Jr. et al. |
| 8,513,621 | B2 | 8/2013 | Nackashi et al. |
| 8,829,469 | B2 | 9/2014 | Damiano, Jr. et al. |
| 8,853,646 | B2 | 10/2014 | Nackashi et al. |
| 8,859,991 | B2 | 10/2014 | Nackashi et al. |
| 8,872,128 | B2 | 10/2014 | Damiano, Jr. et al. |
| 8,872,129 | B2 | 10/2014 | Damiano, Jr. et al. |
| 8,920,723 | B2 | 12/2014 | Damiano, Jr. et al. |
| 9,040,939 | B2 | 5/2015 | Damiano, Jr. et al. |
| 9,048,065 | B2 | 6/2015 | Damiano et al. |
| 9,064,672 | B2 | 6/2015 | Mick et al. |

(Continued)

OTHER PUBLICATIONS

PCT, International Search Report for International Patent Application No. PCT/US2016/049666 dated Dec. 1, 2016.

(Continued)

*Primary Examiner* — Kiet T Nguyen
(74) *Attorney, Agent, or Firm* — NK Patent Law

(57) ABSTRACT

A heating device having a heating element patterned into a robust MEMs substrate, wherein the heating element is electrically isolated from a fluid reservoir or bulk conductive sample, but close enough in proximity to an imagable window/area having the fluid or sample thereon, such that the sample is heated through conduction. The heating device can be used in a microscope sample holder, e.g., for SEM, TEM, STEM, X-ray synchrotron, scanning probe microscopy, and optical microscopy.

20 Claims, 12 Drawing Sheets

(56) References Cited

U.S. PATENT DOCUMENTS

| | | |
|---|---|---|
| 9,275,825 B2 | 3/2016 | Damiano et al. |
| 9,275,826 B2 | 3/2016 | Damiano, Jr. et al. |
| 9,312,097 B2 | 4/2016 | Nackashi et al. |
| 9,324,539 B2 | 4/2016 | Damiano, Jr. et al. |
| 9,437,393 B2 | 9/2016 | Damiano, Jr. et al. |
| 9,466,459 B2 | 10/2016 | Gardiner et al. |
| 2004/0099057 A1 | 5/2004 | Hornung et al. |
| 2010/0103216 A1 | 4/2010 | Silverbrook et al. |
| 2011/0079710 A1* | 4/2011 | Damiano, Jr. .......... H01J 37/20 250/307 |
| 2013/0264476 A1 | 10/2013 | Damiano, Jr. et al. |
| 2014/0138558 A1 | 5/2014 | Damiano, Jr. et al. |
| 2015/0129778 A1* | 5/2015 | Nackashi ................ H01J 37/20 250/453.11 |
| 2015/0179397 A1 | 6/2015 | Damiano, Jr. et al. |

OTHER PUBLICATIONS

PCT, Written Opinion of the International Searching Authority for International Patent Application No. PCT/US2016/049666 dated Dec. 1, 2016.

WIPO, International Preliminary Report on Patentability for PCT Patent Application No. PCT/US2016/049666, dated Mar. 6, 2018.

* cited by examiner

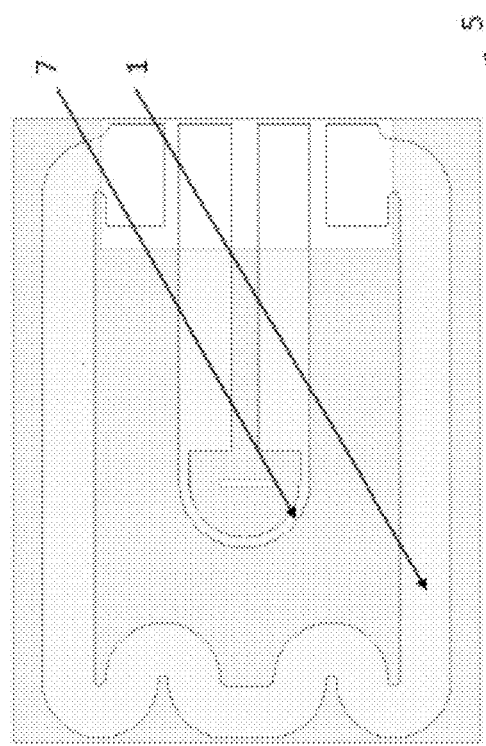
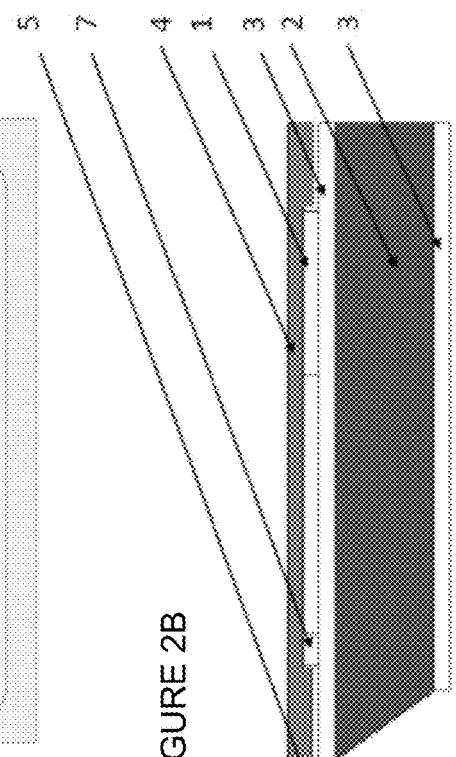
FIGURE 2A
FIGURE 2B
FIGURE 2C

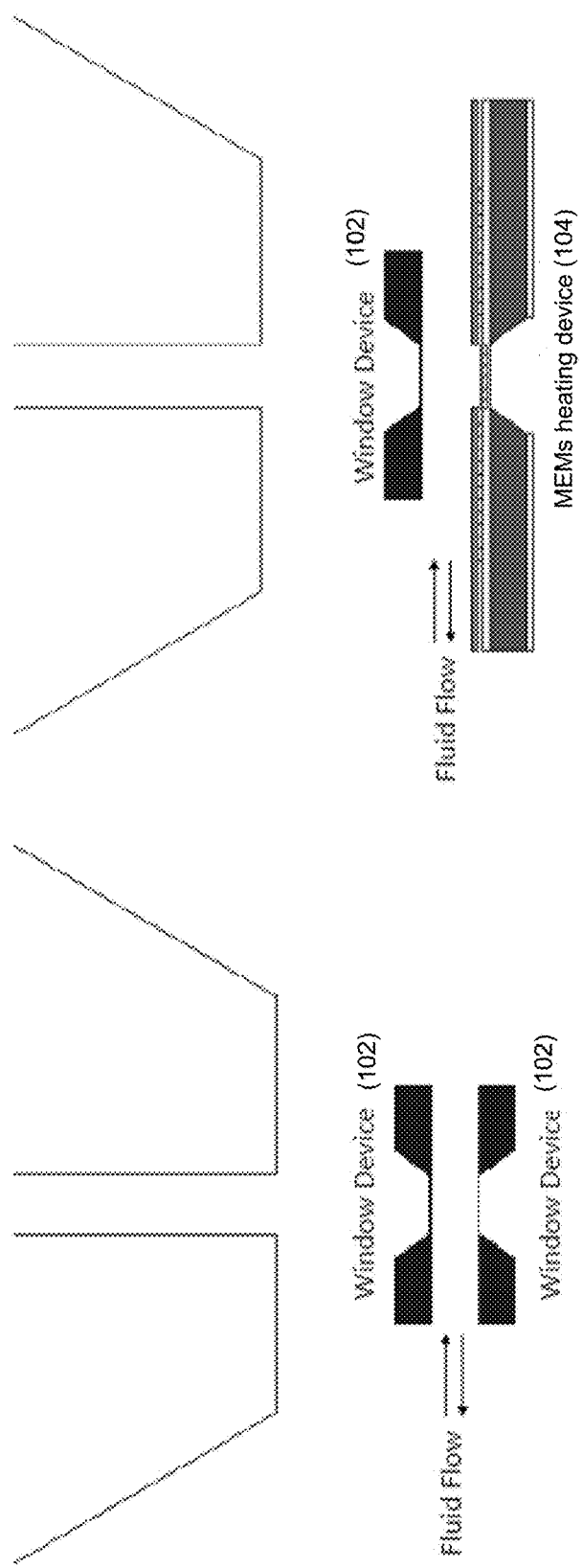

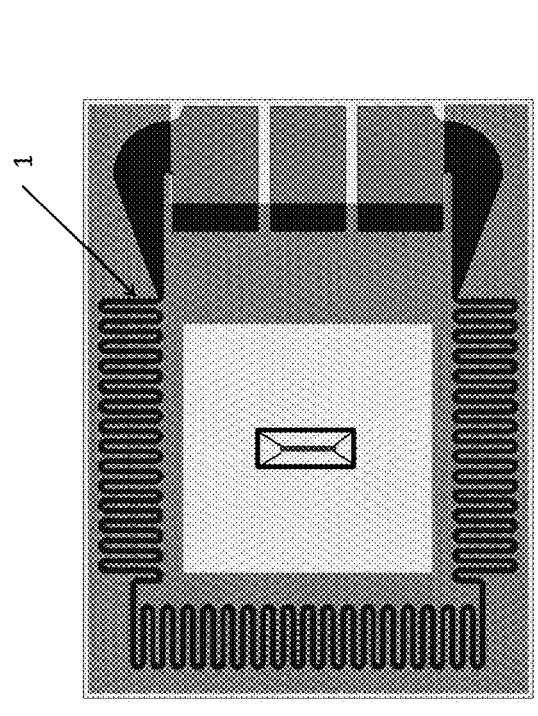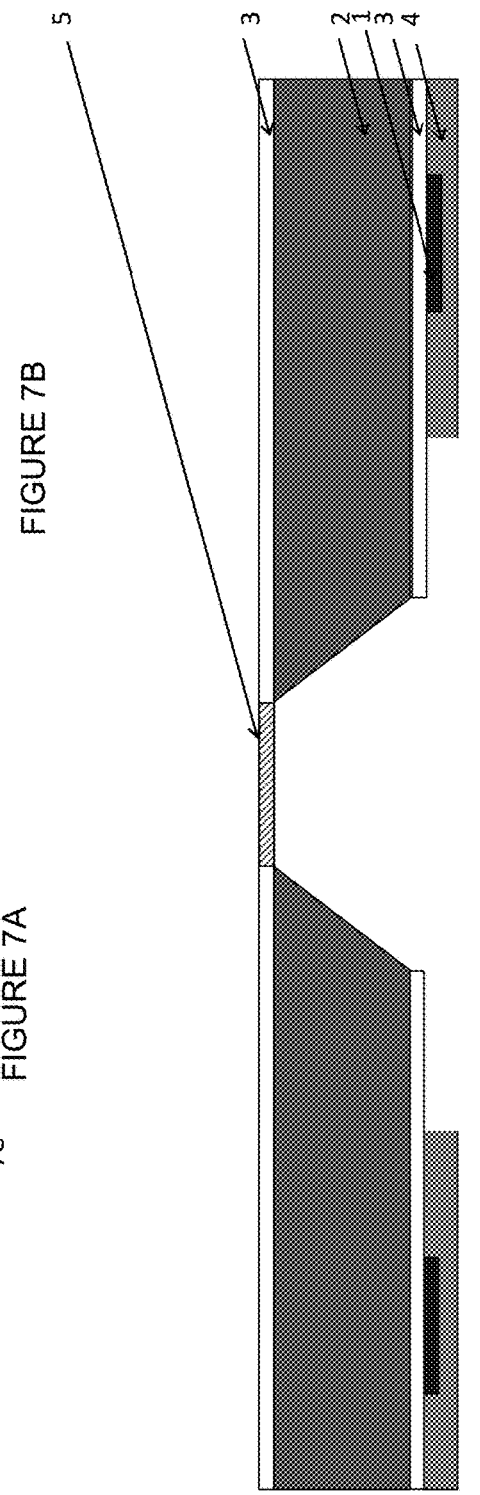
FIGURE 7A
FIGURE 7B
FIGURE 7C

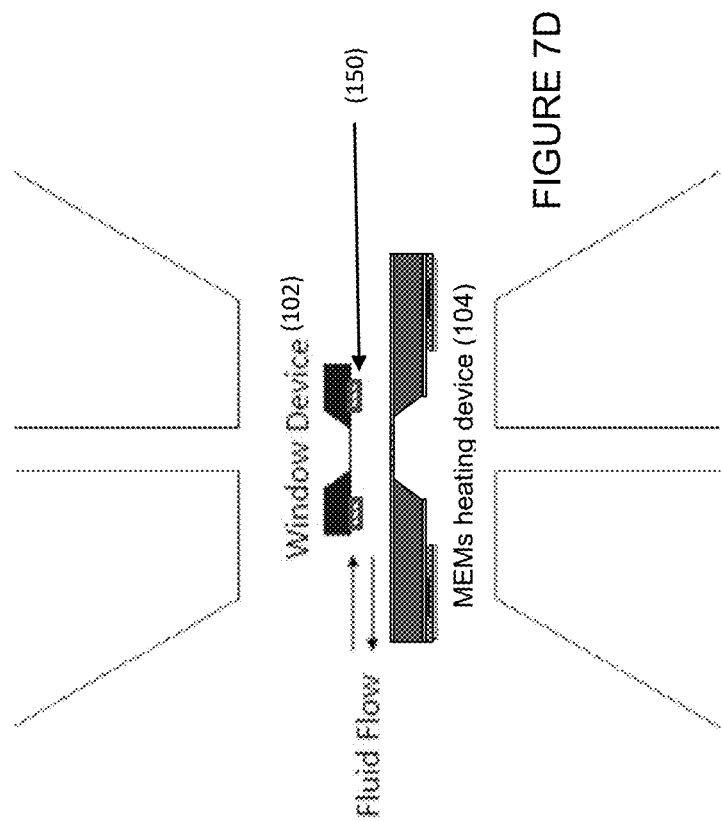

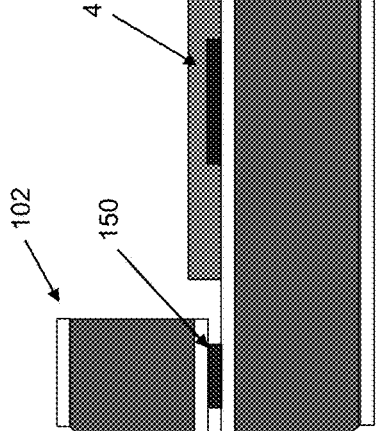
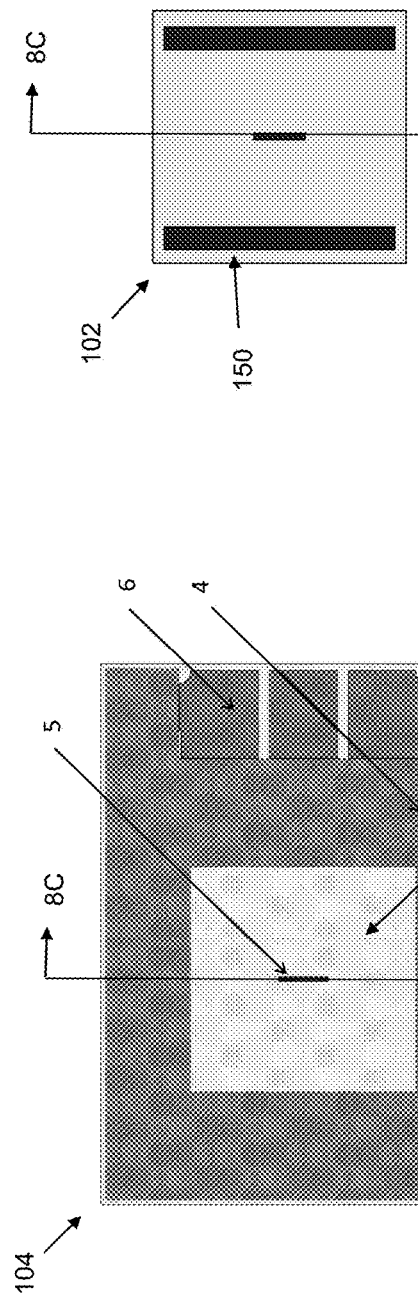
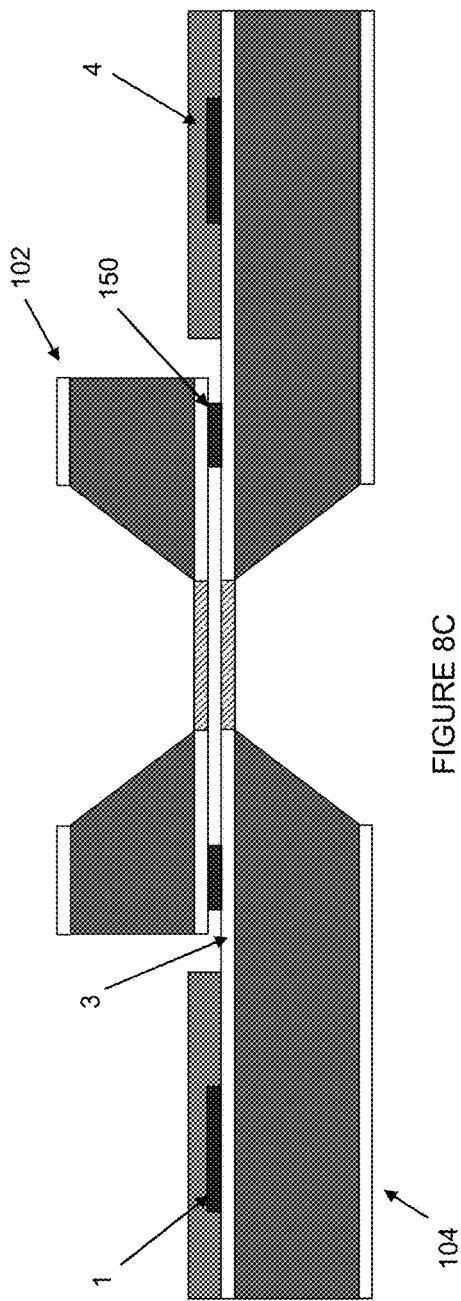

MEMS FRAME HEATING PLATFORM FOR ELECTRON IMAGABLE FLUID RESERVOIRS OR LARGER CONDUCTIVE SAMPLES

CROSS-REFERENCE TO RELATED APPLICATIONS

This application is filed under the provisions of 35 U.S.C. § 111(a) and claims priority to U.S. Provisional Patent Application No. 62/212,241 filed on Aug. 31, 2015, which is hereby incorporated by reference herein in its entirety.

FIELD

The invention relates generally to a heating device patterned onto a robust MEMs substrate for heating a fluid reservoir or bulk conductive sample.

BACKGROUND

The present applicant had previously disclosed on-window MEMs heaters, wherein the device has a membrane region that is heatable and imagable, allowing the user to heat and image a sample in real time with increased accuracy. Disadvantageously, larger conductive samples or fluid reservoirs, i.e., environmental cells, require an increased power, thermal stability under different conditions of fluid flow, thermal uniformity, and electrical isolation not achievable with on-window MEMs heaters. Accordingly, a device comprising heater elements is needed for heating enclosed fluid reservoirs or heating larger conductive samples inside of an electron microscope.

Typical bulk heaters cannot be patterned onto the MEMs sample support and are usually a separate component. These bulk heaters are not easily serviceable and are typically further removed from the sample position requiring more power output than necessary and increased sample drift during imaging due to more thermal expansion. Being further removed from the sample position the heater is not very responsive to sample temperature and the element impedance cannot be used as a reliable sensor of sample temperature.

U.S. Patent Application Publication No. 20080179518 in the name of Creemer et al. relates in part to an on-window heating coil solution. Creemer et al. placed the heating coils in the middle of the observation window only, which will locally heat the fluid around the heating coils but there will also be significant thermal degradation further away from the coils. Creemer et al. does not conduct thermal energy into the support frame of their device. Another disadvantage of the Creemer et al. application is that with an on-membrane heater, the stresses on the membrane are considerably more.

Accordingly, a device is needed that provides the power, thermal stability and uniformity, and electrical isolation of a typical bulk heater as well as the proximity, serviceability, thermal response, and wafer scale benefits of a MEMs heater.

SUMMARY

The invention disclosed herein generally relates to a MEMS heating device for heating a sample, e.g., in an environmental cell, in a microscope sample holder, e.g., for SEM, TEM, STEM, X-ray synchrotron, scanning probe microscopy, and optical microscopy.

In one aspect, a MEMS heating device is described, said device comprising:
(a) at least one observation region,
(b) a thermally conductive structural frame which supports and flanks the observation region,
(c) at least one heat source element supported by the thermally conductive structural frame, wherein the at least one heat source element flanks but does not contact the at least one observation region,
wherein the thermally conductive structural frame is heated by the at least one heat source element.

In another aspect, a microscope device is described, said microscope device comprising a MEMS heating device mounted in a manner which permits microscopic imaging of a sample on the device wherein the at least one heat source element is coupled to a source of electricity, and wherein the MEMS heating device comprises:
(a) at least one observation region,
(b) a thermally conductive structural frame which supports and flanks the observation region,
(c) at least one heat source element supported by the thermally conductive structural frame, wherein the at least one heat source element flanks but does not contact the at least one observation region,
wherein the thermally conductive structural frame is heated by the at least one heat source element.

In still another aspect, a method of imaging a sample at multiple temperatures and/or while changing temperatures using an in situ microscope device is described, the method comprising providing a MEMS heating device, positioning the sample on the membrane at the observation region of said device, and controlling the temperature of the system during imaging, and wherein the MEMS heating device comprises:
(a) at least one observation region,
(b) a thermally conductive structural frame which supports and flanks the observation region,
(c) at least one heat source element supported by the thermally conductive structural frame, wherein the at least one heat source element flanks but does not contact the at least one observation region,
wherein the thermally conductive structural frame is heated by the at least one heat source element.

In yet another aspect, an environmental cell comprising a MEMS heating device configured to permit control of:
(a) heating of a sample on the observation region of the device through conduction from the thermally conductive structural frame; and
(b) heating of one or more other environmental conditions of the sample on the device, wherein the one or more environmental conditions is selected from the group consisting of liquid content and gas content,
and wherein the MEMS heating device comprises:
(a) at least one observation region,
(b) a thermally conductive structural frame which supports and flanks the observation region,
(c) at least one heat source element supported by the thermally conductive structural frame, wherein the at least one heat source element flanks but does not contact the at least one observation region,
wherein the thermally conductive structural frame is heated by the at least one heat source element.

Other aspects, features and embodiments of the invention will be more fully apparent from the ensuing disclosure and appended claims.

BRIEF DESCRIPTION OF THE FIGURES

FIG. 2A illustrates a top view of a second embodiment of the device.

FIG. 2B illustrates a top view of the device of FIG. 2A without the covering dielectric (4) in order to show the heat source element and the secondary sensing element.

FIG. 2C illustrates a cross-section view of the device of FIG. 2A at line 2C-2C'.

FIG. 6A illustrates a cross-sectional view of an environmental cell (E-cell) formed using two window devices.

FIG. 6B illustrates a cross-sectional view of an environmental cell (E-cell) formed using one window device (102) and one MEMs heating device (104).

FIG. 7A illustrates a bottom view of a fourth embodiment of the device.

FIG. 7B illustrates a bottom view of the device of FIG. 7A without the covering dielectric (4) in order to show the heat source element.

FIG. 7C illustrates a cross-section view of the device of FIG. 7A at line 7C-7C'.

FIG. 7D illustrates a cross-sectional view of environmental cell (E-cell) formed using a MEMs heating device of FIGS. 7A-7C and a window device.

FIG. 8A illustrates the MEMS heating device (104) of FIG. 3A.

FIG. 8B is a top view of a window device (102), complete with at least one spacer (150).

FIG. 8C is a cross-section of the window device (102) of FIG. 8B positioned on the MEMS heating device of FIG. 8A, illustrating the "nestled" placement of the window device on the MEMS heating device.

DETAILED DESCRIPTION

Figure 1A:
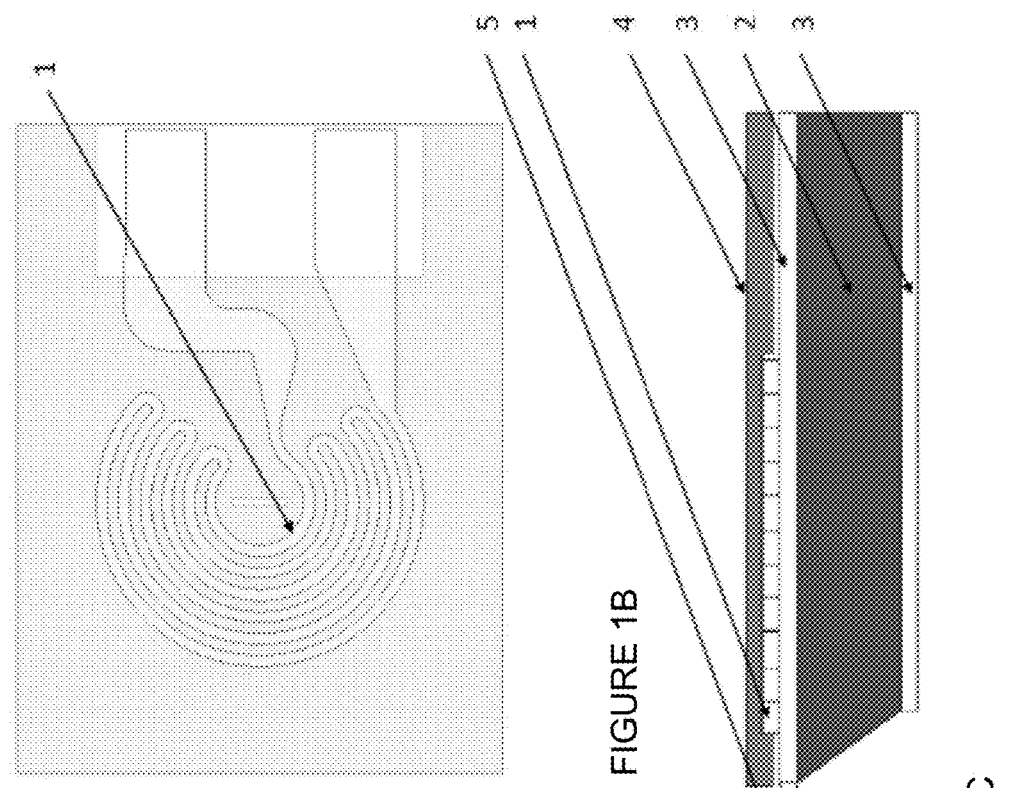
FIG. 1A illustrates a top view of a first embodiment of the device.

The device described herein comprises a heating element patterned into a robust MEMs substrate, wherein the heating element is electrically isolated from a fluid reservoir or bulk conductive sample, but close enough in proximity to an imagable window/area having the fluid or sample thereon, such that the sample is heated through conduction. The heating element on the MEMs substrate is isolated by very thin films so that it can accurately heat the sample or fluid while being responsive to system temperature. The MEMs heating device described herein can be inserted into a microscope sample holder, e.g., for SEM, TEM, STEM, X-ray synchrotron, scanning probe microscopy, and optical microscopy.

As defined herein, a "window device" means a device used to create a physical, electron transparent barrier on one boundary and the vacuum environment of the electron microscope and is generally a silicon nitride-based semiconductor micro-machined part, although other semiconductor materials are contemplated.

As defined herein, "frame" means a rigid region around the perimeter of a device that is used to provide mechanical support to the entire device structure.

As defined herein, "membrane region" or "observation region" for TEM applications means a region generally in the center of each device that is unsupported by the frame, e.g., in a window device the membrane region may be a thin, amorphous silicon nitride film that is electron transparent. For SEM, X-ray synchrotron, scanning probe microscopy, and optical microscopy applications, the "observation region" doesn't require a thin membrane and is generally in proximity to the heat source elements described herein.

As described herein, the "sample holder" is a component of an electron microscope providing the physical support for specimens under observation. Sample holders traditionally used for TEMs and STEMs consist of a rod that is comprised of three key regions: the end, the barrel and the sample tip. In addition to supporting the sample, the sample holder provides an interface between the inside of the instrument (i.e., a vacuum environment) and the outside world. To use the sample holder, at least one device is inserted into the sample tip. The sample holder is inserted into the electron microscope through a load-lock. During insertion, the sample holder is pushed into the electron microscope until it stops, which results in the sample tip of the sample holder being located in the column of the microscope. At this point, the barrel of the sample holder bridges the space between the inside of the microscope and the outside of the load lock, and the end of the sample holder is outside the microscope. The exact shape and size of the sample holder varies with the type and manufacturer of the electron microscope, but each holder contains these three key regions. The "sample holder" for most common SEMs as well as other microscopy instruments such as scanning probe microscopy, X-ray synchrotron and light optical microscopy corresponds to a structure that fixtures a device and mates to a stage on the specified microscopy instrument. This structure may not have the three key regions typically used for TEMs and STEMs, but it serves the same function to support the sample and provide an interface between the inside of the instrument and the outside world. For each of these microscopy instruments the means by which the mount enters the inside of the microscope and how it is stabilized in the microscope varies with the type and manufacturer of the microscope. The sample holder can also be used to provide stimulus to the specimen, and this stimulus can include temperature, electrical current, electrical voltage, mechanical strain, etc.

Heating elements are electrically driven and as such, an insulating layer is necessary to prevent electrical conduction through the sample or fluid which would cause an electrical short or an alternative current pathway. Disadvantageously, in the prior art, the electrically insulated layer required the isolation of the heating elements from the larger conductive samples or fluid reservoirs which would decrease the attainable resolution over the imagable window. In order to effectively heat the larger conductive sample or fluid reservoir, a heating element off of the delicate, imagable window has been used.

Figure 1B:
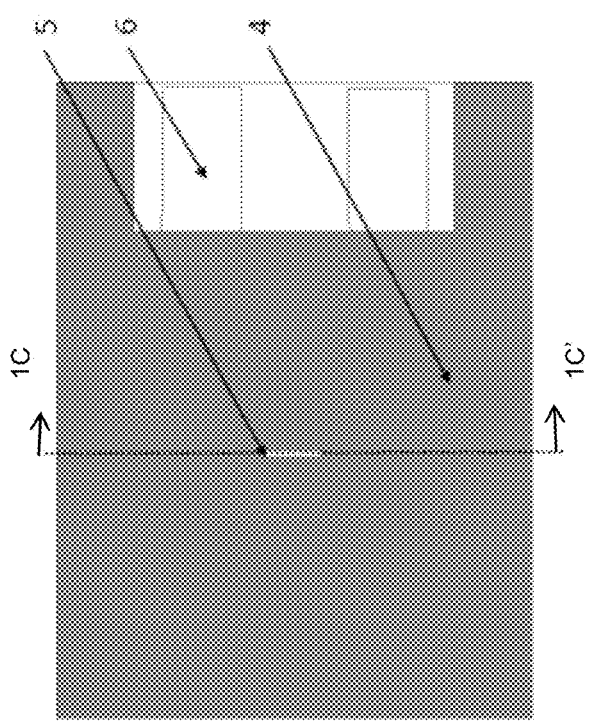
FIG. 1B illustrates a top view of the device of FIG. 1A without the covering dielectric (4) in order to show the heat source element (1).
Figure 1C:
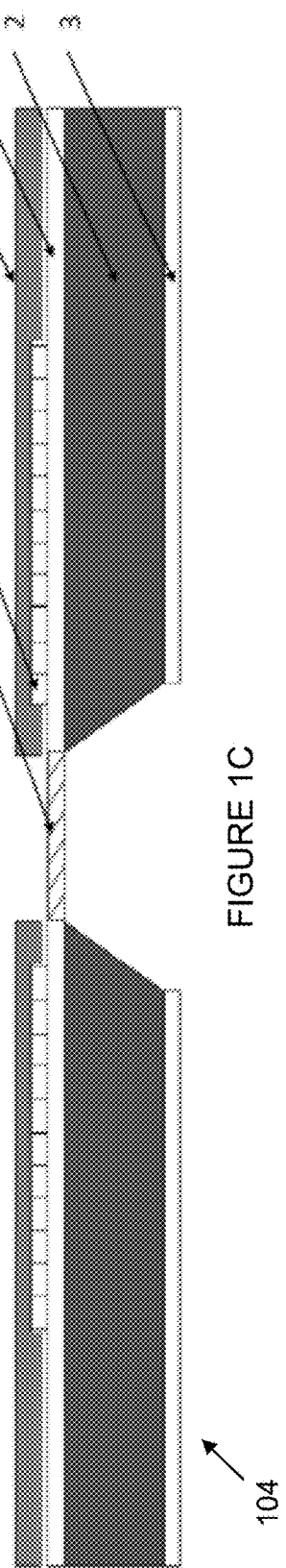
FIG. 1C illustrates a cross-section view of the device of FIG. 1A at line 1C-1C'.

FIG. 1 illustrates a first embodiment of the MEMs heating device (104) described herein wherein at least one heat source element (1) is electrically insulated from the thermally conductive structural frame (2) by a thin dielectric (3) and electrically insulated from any one or more environmental conditions exposed to the device by a covering dielectric (4). The at least one heat source element (1) is arranged so that thermal energy can be efficiently conducted into the thermally conductive structural support frame (2) and then further conducted in a stable and uniform manner to the at least one observation region (5) which is a thin continuous membrane. Importantly, the heat source element (1) flanks but does not directly contact the observation region (5). The at least one heat source element can be easily electrically accessible using at least two exposed conductive contacts (6). FIG. 1A illustrates a top view of a first embodiment of the device. FIG. 1B illustrates a top view of the device of FIG. 1A without the covering dielectric (4) in order to show the shape and positioning of the heat source element (1). FIG. 1C illustrates a cross-section view of the device of FIG. 1A at line 1C-1C'. Advantageously, the MEMs heating device can be constructed using semiconductor materials using semiconductor manufacturing processes (e.g., lithography) and can be readily interchanged with another sample support device (e.g., a window device or a temperature control device). As shown in FIG. 1, the at least one heat source element is patterned directly onto a thin dielectric (3) in contact with the thermally conductive structural frame (2), although it is envisioned that the at least one heat source element can be patterned into a thin dielectric, as readily understood by the person skilled in the art. Although not shown, it is contemplated herein that the at least one heat source element (1) can be patterned directly onto the thermally conductive structural frame (2). Regardless, the at least one observation region (5) is positioned so that thermal energy can be conducted from the frame (2) into the observation region (5).

The heat source element (1) can be any metal or ceramic heating element including, but not limited to, tungsten, platinum, tantalum, rhenium, molybdenum, titanium, nichrome, kanthal, cupronickel or any other metal heater, preferably tungsten and platinum. Ceramic heaters contemplated include any number of polysilicon heaters, silicide heaters, nitride heaters or carbide heaters including silicon carbide, titanium carbide, molybdenum disilicide, molybdenum carbide, tungsten carbide, tungsten nitride, tantalum nitride, boron nitride, FeCrAl, NiCr, titanium silicide, tantalum silicide, cobalt silicide, titanium nitride, and aluminum nitride. It should be appreciated that the heat source element should be stable at high temperatures and shouldn't evaporate or react with other materials. The thickness of the heat source element is 0.00001-5 µm, preferably 100-200 nm.

The conductive structural frame (2) can be any semiconductor material, metal or ceramic support structure, preferably a good thermal conductor. Preferred embodiments include a silicon frame selectively etched using KOH, a silicon frame selectively etched using reactive ion etching (RIE), a silicon frame selectively etched using deep reactive ion etching (DRIE), or a silicon frame released from an silicon-on-insulator (SOI) wafer. It should be appreciated that the frame material must be able to withstand high temperature deposition processes for the heater, membrane, and thin dielectric layers, and must be etched selectively relative to the materials used for the heater, membrane, and thin dielectric. The thickness of the conductive structural frame is in a range from 0.00001-1 mm, preferably 200-300 µm.

It should be appreciated that the thin dielectric (3) can be the same as or different than the covering dielectric (4). Dielectric materials include, but are not limited to, any material having a dielectric constant less than about 4. Preferably, the dielectric materials include low-polarity materials such as silicon-containing organic polymers, silicon-containing hybrid organic/inorganic materials, organosilicate glass (OSG), TEOS, fluorinated silicate glass (FSG), silicon dioxide, silicon nitride, alumina, photoresists such as SU8 (a negative, epoxy-type, near-UV photoresist) and carbon-doped oxide (CDO) glass. It is to be appreciated that the dielectric materials may have varying densities and varying porosities. The thickness of the dielectric materials is preferably in a range from 0.00001-5 µm. In a preferred embodiment, the thin dielectric (3) comprises about 1-100 nm thick silicon nitride and the covering dielectric comprises 100-1000 nm thick SU-8. In one embodiment, the thin dielectric (3) comprises the same material as the covering dielectric (4). In another embodiment, the thin dielectric (3) comprises a different material than the covering dielectric (4). In still another embodiment, the thin dielectric (3) comprises the same material as the covering dielectric (4), but the porosity and/or density, and hence the dielectric constant, is different. Most preferably, the thin dielectric (3) comprises silicon nitride and the covering dielectric comprises SU8. Alternatively, the thin dielectric may be LPCVD nitride, while the covering dielectric comprises PECVD nitride deposited at a lower temperature.

The observation region (5) is a membrane, the makeup of which is dependent on the type of microscopy being practiced. For example, with transmission electron microscopy both an open cell and a closed environmental cell requires the observation region to be a thin membrane that is supported by the frame including, but not limited to, amorphous silicon nitride, silicon carbide, boron nitride, graphene, carbon, aluminum nitride, silicon dioxide and silicon, preferably silicon nitride. For SEM, X-ray synchrotron, scanning probe microscopy, and optical microscopy, the observational region doesn't require a thin membrane and as such, a non-conductive sample can be placed directly on the structural support frame (2), dielectric, or heat source element (1). In other words, for SEM, X-ray synchrotron, scanning probe microscopy, and optical microscopy, the observation region (5) of FIG. 1 can comprise the same material as the thin dielectric (3). Regardless of the application, the observation region may either be comprised of a continuous film or material or may be comprised of a stack of films or materials, or may contain one or more holes perforating the membrane from the top to the bottom surface, or may contain one or more dimples in its top or bottom surface. Holes perforating the membrane are generally less than 10 microns across, but can be as large as hundreds of microns. Holes are generally circular in shape, but may also be squares, diamonds, rectangular, triangular or polygonal. Holes are generally used to create regions in a membrane region that are completely electron transparent, upon which a sample can be placed. Dimples in the membrane material within the membrane region are generally less than 100 microns across, but can be as large as hundreds of microns. Dimples are generally circular in shape, but may also be squares, diamonds, rectangular, triangular or polygonal. Dimples are generally used to create regions in a membrane region that are relatively more electron transparent than the non-dimpled membrane regions. The thickness of the observation region is 0.00001-1 μm, preferably 50-200 nm, and more preferably 10-100 nm. The size of the observation region is in a range x times y of from about (10 nm-10 mm) times (10 nm-10 mm), depending on the microscopy practiced. Preferably, the observation region is in a range from about 100-700 μm times 10-100 μm.

The exposed conductive contacts (6) include a coating such as solder, nickel/gold, or some other anti-corrosive coating.

It should be appreciated that the heat source element (1) flanks but does not contact the at least one observation region. As shown in FIG. 1, the heat source element resembles an electric oven element but the heat source element can be arranged in any shape necessary to ensure the heating device heats the observation region and sample to the temperatures necessary, e.g., FIG. 2B. For example, the shape of the heat source element can be a serpentine winding pattern, a concentric coil pattern, a simple circle around the observation region, a meandering trace, a direct trace, or any combination thereof. For metal heat source element, it is preferred that the trace be thinner while for ceramic heat source elements, the trace can be much wider. Further, the heat source element (1) is not in the line of the electron beam, i.e., the observation region (5), but instead positioned over the conductive structural frame (2) so as to adequately heat the frame for conduction to the observation region (5). If the heat source element (1) were in the observation region (5), e.g., in the Creemer et al. application, localized heating around the heat element would cause a less uniform temperature profile across the observation region, which can be amplified in liquids. The frame of the present device has a larger surface contact with the fluid or bulk sample and since the frame is a very thermally conductive material it heats the fluid or observation region up more uniformly even under fluid flow conditions. Further, the observation region of the present device isn't large enough to pattern a heat source element that will be able to safely deliver enough power to fully heat up the fluid or conductive sample. A heat source element on the observation region, e.g., Creemer et al., can also be more dangerous because the stresses on the membrane will be greater and if the heater were to fail, the window of the E-cell is more likely to fail releasing the enclosed liquid or gas into the microscope. A patterned heat source element creates a non-uniform temperature profile across the surface of the supporting substrate, i.e., higher temps at the heater element and lower temps between and surrounding the heater elements. By placing these elements on the relatively thick frame rather than the thin membrane, the higher temperatures and the stresses imparted to the supporting substrate are much less likely to cause failure as the thicker frame is less likely to fracture or otherwise become damaged from the stresses. When heating the frame, the temperature and the stresses on the membrane are lower and uniform. The heating element in the observation region can also physically restrict viewing certain locations on the observation region. Heating the frame up allows the accurate use of the impedance of the heating element or an optional secondary sense element to measure the temperature of the system since it is on a stable heat sink that will represent the temperature of the sample and the fluid. In addition, a covering dielectric is used to electrically isolate the heat element from the sample or fluid, which could limit resolution by further scattering the electrons during transmission.

FIG. 2 illustrates a second embodiment of the MEMs heating device (104) described herein wherein at least one secondary sense element (7) is patterned on or near the observation area or on the thermally conductive frame and has a known thermal impedance which is used to monitor the temperature of the device. It is noted that the MEMs heating device of the second embodiment can be designed without the at least one secondary sense element (7). When present, the secondary sense element (7) can also act as a heat source element. FIG. 2A illustrates a top view of a second embodiment of the device. FIG. 2B illustrates a top view of the device of FIG. 2A without the covering dielectric (4) in order to show the heat source element and the secondary sensing element. FIG. 2C illustrates a cross-section view of the device of FIG. 2A at line 2C-2C'. Advantageously, the MEMs heating device can be constructed using semiconductor materials using semiconductor manufacturing processes (e.g., lithography) and can be readily interchanged with another sample support device (e.g., a window device or a temperature control device). As shown in FIG. 2, the at least one heat source element is patterned directly onto a thin dielectric (3) in contact with the thermally conductive structural frame (2), although it is envisioned that the at least one heat source element can be patterned into a thin dielectric, as readily understood by the person skilled in the art. Although not shown, it is contemplated herein that the at least one heat source element (1) can be patterned directly onto the thermally conductive structural frame (2). Regardless, the at least one observation region (5) is positioned so that thermal energy can be conducted from the frame (2) into the observation region (5).

Figure 3B:
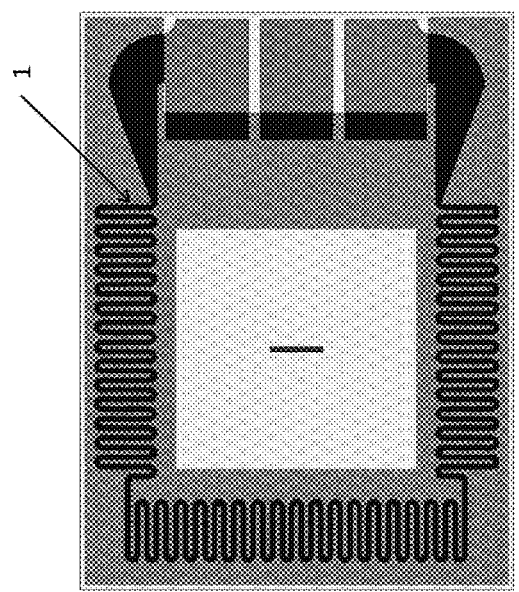
FIG. 3B illustrates a top view of the device of FIG. 3A without the covering dielectric (4) in order to show the heat source element.
Figure 3A:
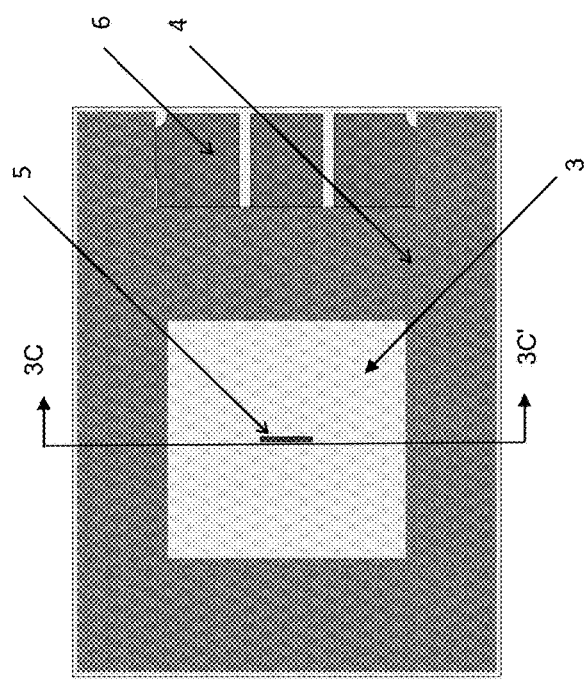
FIG. 3A illustrates a top view of a third embodiment of the device.
Figure 3C:
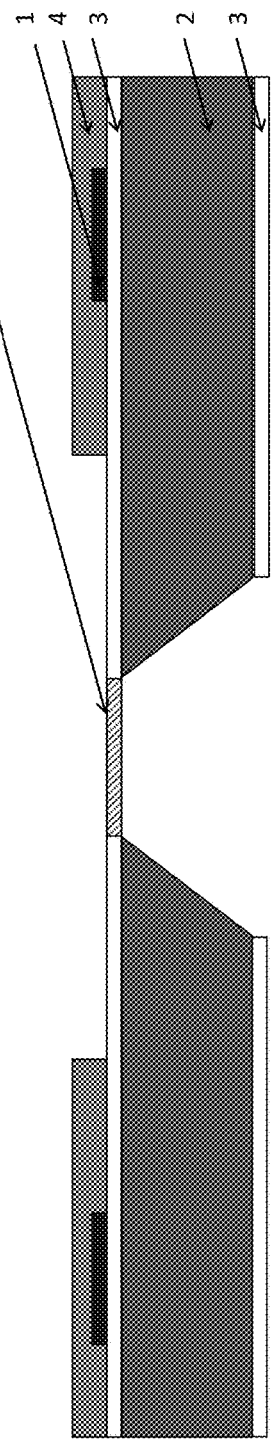
FIG. 3C illustrates a cross-section view of the device of FIG. 3A at line 3C-3C'.

FIG. 3 illustrates a third embodiment of the MEMs heating device (104) described herein. It is noted that the MEMs heating device of the third embodiment can be designed with at least one secondary sense element (7), although said secondary sense element is not shown in FIG. 3. FIG. 3A illustrates a top view of a third embodiment of the device. FIG. 3B illustrates a top view of the device of FIG. 3A without the covering dielectric (4) in order to show the heat source element. FIG. 3C illustrates a cross-section view of the device of FIG. 3A at line 3C-3C'. It can be seen that the at least one heat source element (1) is in a serpentine pattern around the perimeter of the device and the covering dielectric forms a frame (hereinafter a "covering dielectric frame") around the perimeter of the device, covering the at least one heat source element. Advantageously, with the serpentine pattern of FIGS. 3A-3C, the width of the metal heat source element is narrower, thereby increasing the resistance of the line as well as increasing the resistance per degree temperature, making it easier to measure and control the temperature. Advantageously, the MEMs heating device can be constructed using semiconductor materials using semiconductor manufacturing processes (e.g., lithography) and can be readily interchanged with another sample support device (e.g., a window device or a temperature control device). As shown in FIG. 3, the at least one heat source element is patterned directly onto a thin dielectric (3) in contact with the thermally conductive structural frame (2), although it is envisioned that the at least one heat source element can be patterned into a thin dielectric, as readily understood by the person skilled in the art. Although not shown, it is contemplated herein that the at least one heat source element (1) can be patterned directly onto the thermally conductive structural frame (2). Regardless, the at least one observation region (5) is positioned so that thermal energy can be conducted from the frame (2) into the observation region (5).

The secondary sense element, when present, can be any metal or ceramic heating element including, but not limited to, tungsten, platinum, nichrome, kanthal, cupronickel or any other metal heater, preferably tungsten and platinum. Ceramic heaters contemplated include any number of polysilicon heaters, silicide heaters, nitride heaters or carbide heaters including silicon carbide, molybdenum disilicide, tungsten carbide, boron nitride, and aluminum nitride. It should be appreciated that the secondary sense element must withstand high temperatures without evaporating or reacting with other materials used in the device. The sense element material will change resistivity over the temperature range, and this change must be reversible (i.e., no hysteresis) when the heat is cycled. The thickness range is 0.00001-5 µm, preferably 100-200 nm.

When a device as described herein is used in a chamber (external or within a microscope) that allows the control of gases and/or liquids at the observation region, it becomes part of an environmental cell (E-cell). When multiple devices are stacked or positioned in a columnar arrangement, small areas or cells are created within voids between adjacent devices. These voids provide a space for gas and/or liquid to be confined and controlled, and provide an opportunity to further control the environment of a specimen placed on one or more of the devices. To prevent leaks, seals can be formed either using components such as washers on the devices themselves, or on the holder. These arrangements also form an environmental cell, or E-cell. Although E-cells may be used outside of an electron microscope, they are generally most useful when placed within an electron microscope to allow changes to the environment to take place while the impact of those changes are observed through imaging and/or analysis. It should be appreciated that a sealed E-cell using just one MEMs heating device sealed against the hardware is useful for SEM, optical microscopy or X-ray synchrotron.

Environmental cells are generally constructed using either two window devices, two MEMs heating devices, or a combination of a window device and a MEMs heating device.

It should be appreciated that the environmental cell is in fluid communication with fluidic inlets and hence the environmental cell can receive liquids and/or gases from an external source and the liquids/and gases are returned from the closed cell to an external source. Alternatively, the liquid and/or gas can be statically trapped within the environmental cell. The environmental cell provides stimuli (e.g., temperature, electricity, mechanical, chemical, gas or liquid, or any combination thereof) to the samples and/or devices. Most preferably, the sample is heated on the MEMs heating device through conduction from the thermally conductive frame or the liquid or gas in contact with the MEMs heating device is heated.

Figure 4:
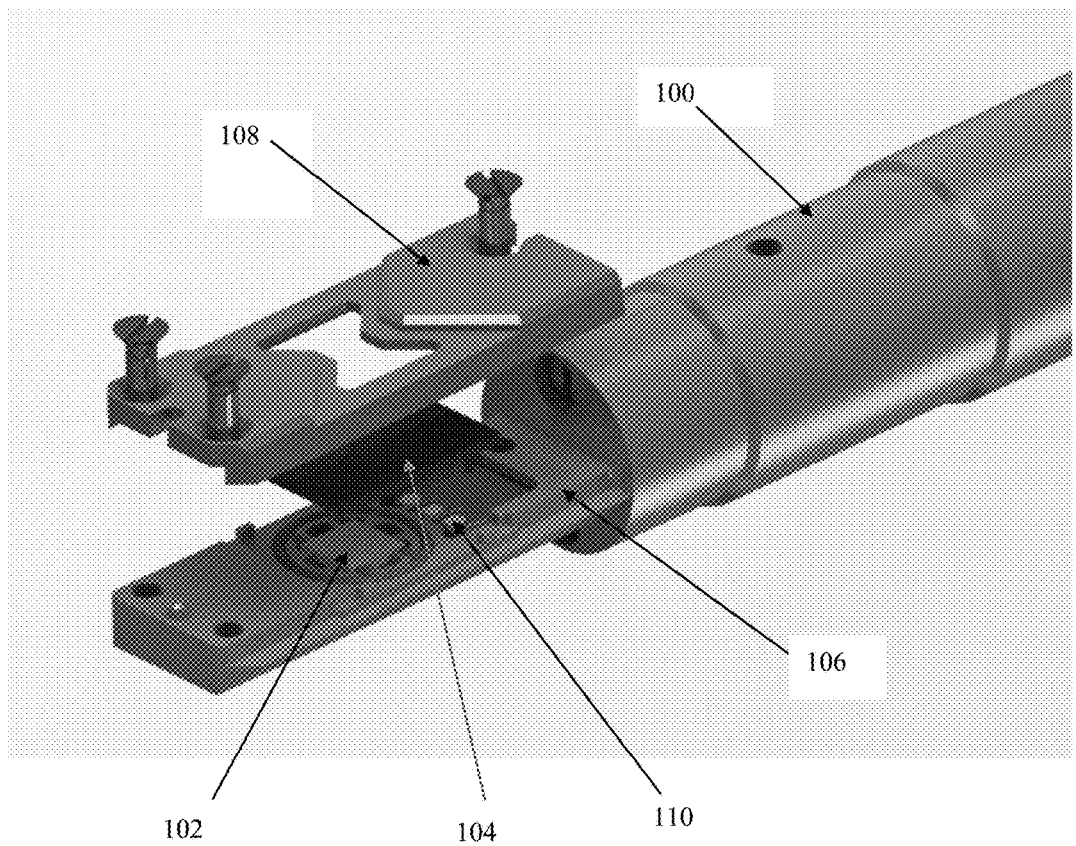
FIG. 4 illustrates an example of the environmental cell, wherein the sample tip (106) of sample holder (100) comprises a window device (102) and the MEMs heating device (104).
Figure 5:
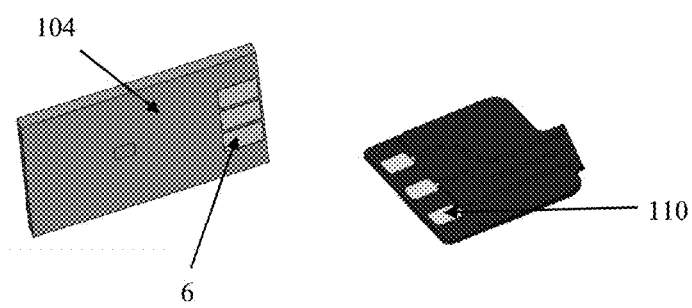
FIG. 5 illustrates the at least one electrode (110) of FIG. 4, wherein it matches the electrical contact points (6) of the MEMs heating device (104).

An example of the environmental cell is shown in FIG. 4, wherein the sample tip (106) of sample holder (100) comprises a window device (102) and the MEMs heating device (104), e.g., of FIG. 1 or 2 or 3 or any embodiment thereof. An embodiment of a sample tip such as this is disclosed in U.S. Pat. No. 8,829,469 issued on Sep. 9, 2014 in the name of John Damiano, Jr., et al. and entitled "ELECTRON MICROSCOPE SAMPLE HOLDER FOR FORMING A GAS OR LIQUID CELL WITH TWO SEMICONDUCTOR DEVICES," which is hereby incorporated by reference in its entirety. In FIG. 4, the electrical contact points (6) of the MEMs heating device (104) are facing down and cannot be seen in this view. The sample tip (106) can include at least one electrode (110) that matches the electrical contact points (6) of the MEMs heating device (104) (see, e.g., FIG. 5). This design allows a MEMs heating device (104) to be mounted quickly and easily, making both physical and electrical contacts, without the need to partially disassemble the sample tip to mount the MEMs heating device, for example, as disclosed in U.S. patent application Ser. No. 14/079,223 filed on Nov. 13, 2013 in the name of John Damiano, Jr., et al. and entitled "A METHOD FOR FORMING AN ELECTRICAL CONNECTION TO A SAMPLE SUPPORT IN AN ELECTRON MICROSCOPE HOLDER," which is hereby incorporated by reference in its entirety. Following loading of the enclosed fluid reservoir or bulk conductive sample and the MEMs heating device (104), a holder lid (108) can be affixed to the sample tip body (106). When the holder lid is affixed to the sample tip body, the electrical contact points (6) of the MEMs heating device (104) press against the electrodes (110) in the sample holder.

FIG. 6 illustrates a cross-sectional view of environmental cells (E-cell) formed using two devices. In FIG. 6A, an environmental cell is shown with two window devices, as an example. In FIG. 6B, an environmental cell is formed using one window device (102) and one MEMs heating device (104), as described herein. It should be appreciated that an environmental cell can comprise two MEMs heating devices, as described herein. Although illustrated to be different sizes, it should be appreciated that the window device and the MEMs heating device can have the same or different dimensions, as necessary for the application.

FIG. 7 illustrates a fourth embodiment of the MEMs heating device (104) described herein wherein at least one heat source element (1) is patterned on the opposite side of the thermally conductive structural support (2) as the observational area (5), wherein the conductive contacts are positioned on the same side of the chip as the heat source element. It is noted that the MEMs heating device of the fourth embodiment can be designed with at least one secondary sense element (7), although said secondary sense element is not shown in FIG. 7. FIG. 7A illustrates a bottom view of a fourth embodiment of the device. FIG. 7B illustrates a bottom view of the device of FIG. 7A without the covering dielectric (4) in order to show the heat source element. FIG. 7C illustrates a cross-section view of the device of FIG. 7A at line 7C-7C'. It can be seen that the at least one heat source element (1) is in a serpentine pattern around the perimeter of the device and the covering dielectric forms a frame (hereinafter a "covering dielectric frame") around the perimeter of the device, covering the at least one heat source element. Advantageously, with the serpentine pattern of FIGS. 7A-7C, the width of the metal heat source element is narrower, thereby increasing the resistance of the line as well as increasing the resistance per degree temperature, making it easier to measure and control the temperature. Advantageously, the MEMs heating device can be constructed using semiconductor materials using semiconductor manufacturing processes (e.g., lithography) and can be readily interchanged with another sample support device (e.g., a window device or a temperature control device). As shown in FIG. 7, the at least one heat source element is patterned directly onto a thin dielectric (3) in contact with the thermally conductive structural frame (2), although it is envisioned that the at least one heat source element can be patterned into a thin dielectric, as readily understood by the person skilled in the art. Although not shown, it is contemplated herein that the at least one heat source element (1) can be patterned directly onto the thermally conductive structural frame (2). Regardless, the at least one observation region (5) is positioned so that thermal energy can be conducted from the frame (2) into the observation region (5). It should be appreciated that the shape and arrangement of the heat source element in FIGS. 7A-7C is analogous to that shown in FIGS. 3A-3C but can be the shape and arrangement of that shown in FIGS. 1A-1C, 2A-2C, or any other shape and arrangement envisioned by those skilled in the art.

FIG. 7D illustrates a cross-section view of environmental cell (E-cell) formed using the MEMS heating this device for FIGS. 7A-7C. It should be appreciated that at least one spacer material (150) is needed on the window device (or the MEMS heating device, not shown) to create a distance between the two devices for liquid flow.

FIG. 8 illustrates one of the advantages of the MEMS heating device of FIGS. 3A-3C, wherein upon formation of the E-cell, a smaller device, e.g., a window device (102), having at least one spacer (150) sits within the "covering dielectric frame" and upon the thin dielectric (3) of the MEMS heating device (104). This has the advantage of minimizing the liquid layer thickness in the closed E-cell because the covering dielectric is no longer deciding the thickness of the liquid layer, e.g., setting the distance, between the two devices. FIG. 8A is the MEMS heating device (104) of FIG. 3A, or equivalent thereof. FIG. 8B is a top view of a window device (102), complete with at least one spacer (150). FIG. 8C is a cross-section of the window device (102) of FIG. 8B positioned on the MEMS heating device of FIG. 8A, illustrating the "nestled" placement of the window device within the covering dielectric frame of the MEMS heating device. As defined herein, the "nestled" placement of the window device on the MEMS heating device corresponds to the placement of the window device within the covering dielectric frame and on the thin dielectric of the MEMS heating device, with some thickness of the covering dielectric (4) circumscribing some portion of the window device, e.g., as shown in FIG. 8C. It should be appreciated that the size of the covering dielectric frame of the MEMS heating device corresponds to the size of the window device to be used.

Figure 9A:
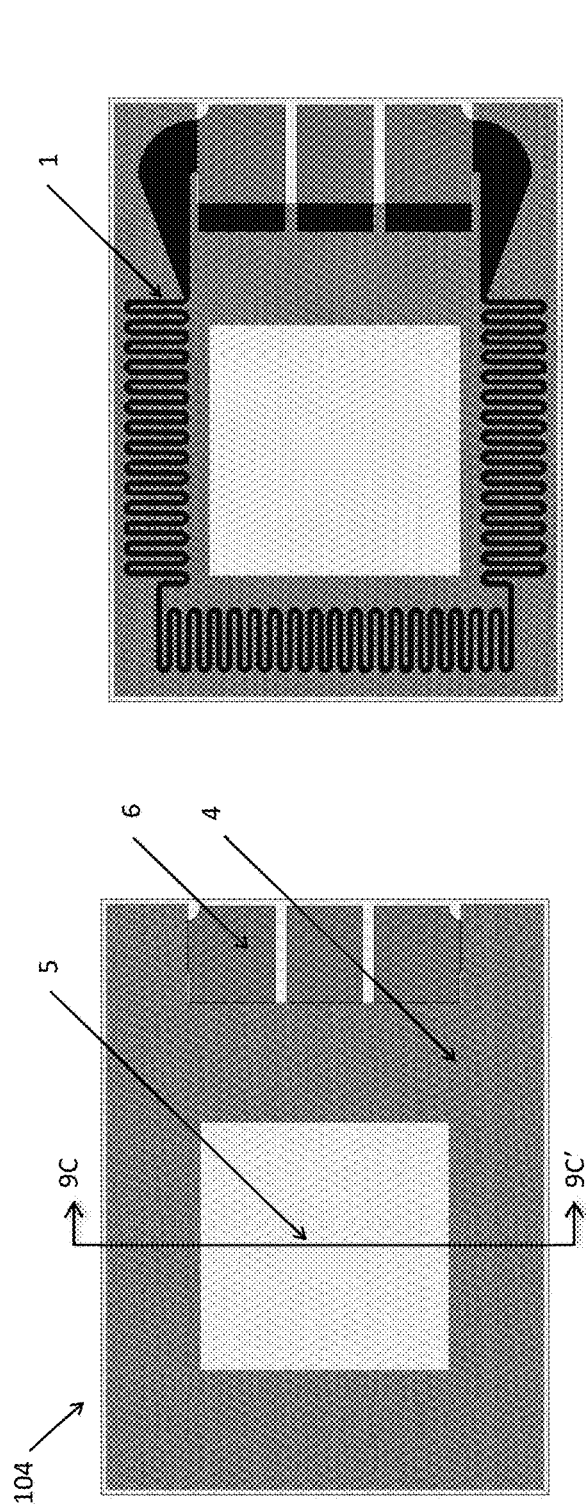
FIG. 9A illustrates a top view of an embodiment of the MEMs heating device wherein the observation region (5) is not a thin continuous membrane.
Figure 9B:
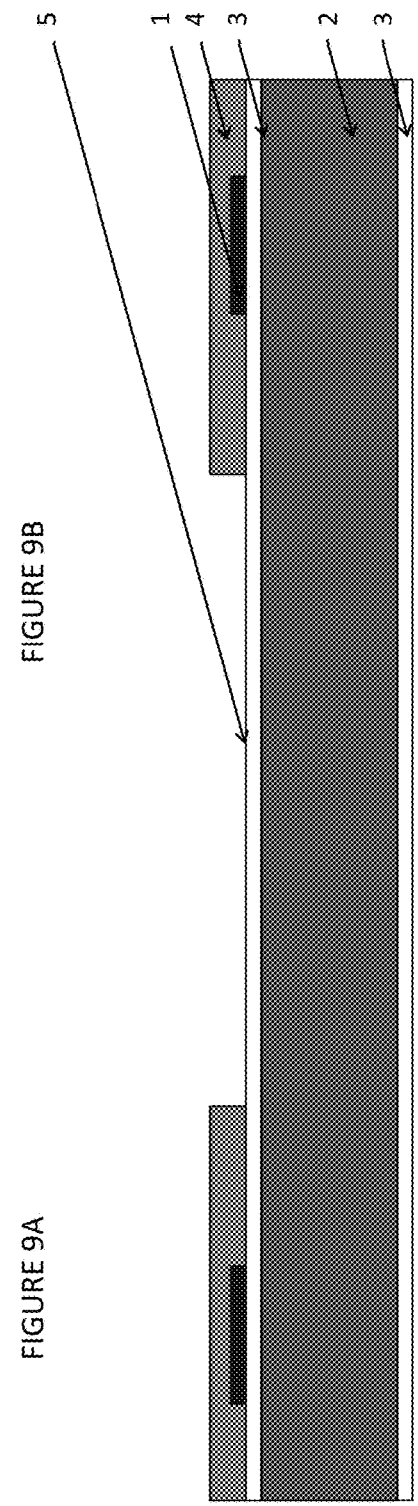
FIG. 9B illustrates a top view of the device of FIG. 9A without the covering dielectric (4) in order to show the heat source element (1).
Figure 9C:
FIG. 9C illustrates a cross-section view of the device of FIG. 9A at line 9C-9C'.

FIG. 9 illustrates an embodiment of the MEMs heating device described herein wherein the observation region (5) is not a thin continuous membrane, for example for SEM, X-ray synchrotron, scanning probe microscopy, and optical microscopy. FIG. 9A illustrates a top view of the device. FIG. 9B illustrates a top view of the device without the covering dielectric (4) in order to show the heat source element (1). FIG. 9C illustrates a cross-section view of the device of FIG. 9A at line 9C-9C', showing the thermally conductive structural support (2) beneath the observation region (5). It should be appreciated that the shape and arrangement of the heat source element in FIGS. 9A-9C is analogous to that shown in FIGS. 3A-3C but can be the shape and arrangement of that shown in FIGS. 1A-1C, 2A-2C, or any other shape and arrangement envisioned by those skilled in the art. Further, it should be appreciated that the covering dielectric in FIGS. 9A-9C is analogous to that shown in FIGS. 3A-3C but can be analogous to that shown in FIG. 1A-1C or 2A-2C. Advantageously, the MEMs heating device can be constructed using semiconductor materials using semiconductor manufacturing processes (e.g., lithography) and can be readily interchanged with another sample support device (e.g., a window device or a temperature control device). As shown in FIG. 9, the at least one heat source element is patterned directly onto a thin dielectric (3) in contact with the thermally conductive structural frame (2), although it is envisioned that the at least one heat source element can be patterned into a thin dielectric, as readily understood by the person skilled in the art. Although not shown, it is contemplated herein that the at least one heat source element (1) can be patterned directly onto the thermally conductive structural frame (2). Regardless, the at least one observation region (5) is positioned so that thermal energy can conduct from the frame (2) into the observation region (5).

Figures 10A, 10B, 10C:
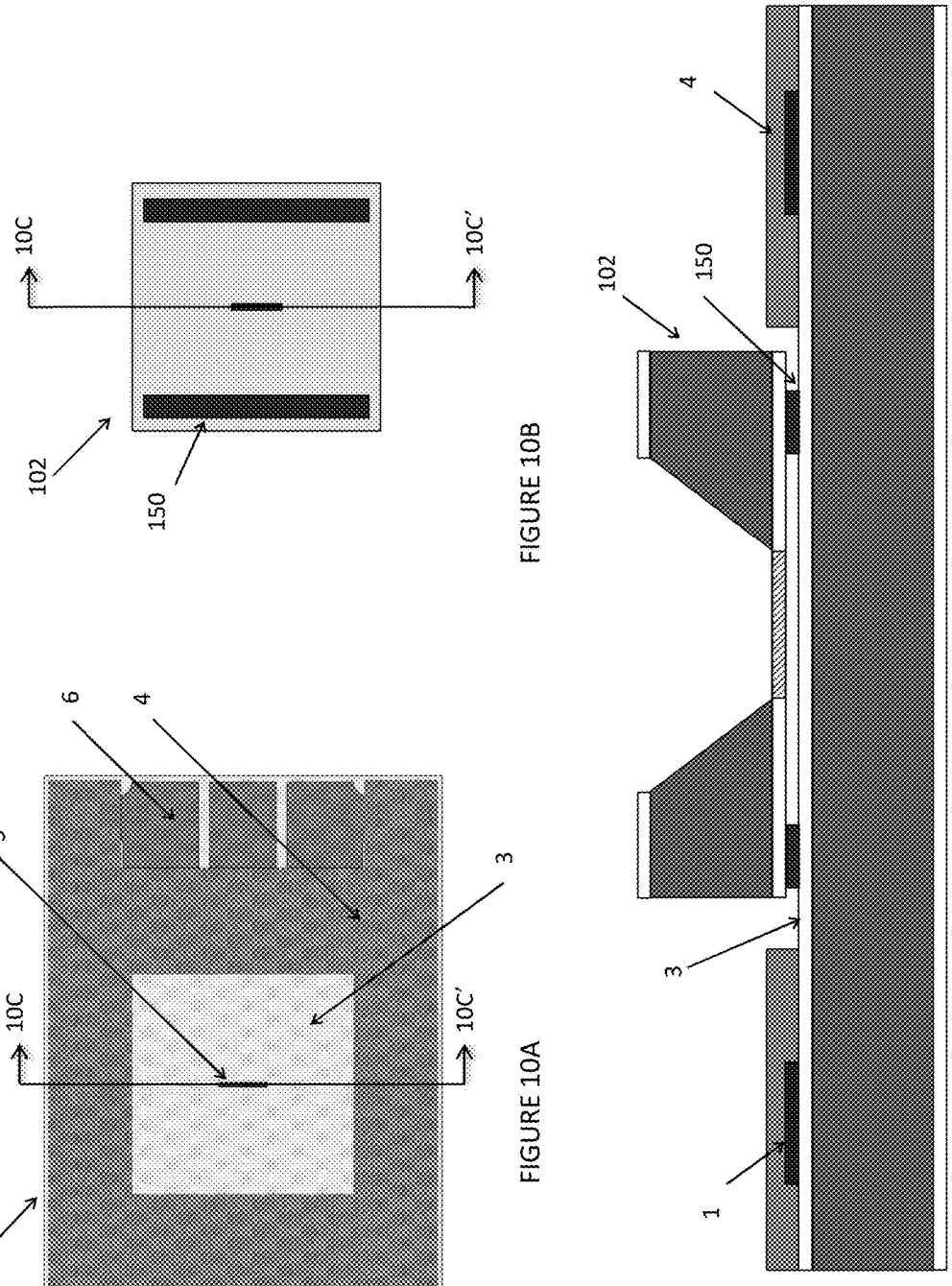
FIG. 10A illustrates the MEMS heating device (104) of FIG. 9A.
FIG. 10B is atop view of a window device (102), complete with at least one spacer (150).
FIG. 10C is a cross-section of the window device (102) of FIG. 10B positioned on the MEMS heating device of FIG. 10A, illustrating the "nestled" placement of the window device on the MEMS heating device.

FIG. 10 illustrates one of the advantages of the MEMS heating device of FIGS. 9A-9C, wherein upon formation of the E-cell, a smaller device, e.g., a window device (102), having at least one spacer (150) sits within the "covering dielectric frame" and upon the thin dielectric (3) of the MEMS heating device (104). This has the advantage of minimizing the liquid layer thickness in the closed E-cell because the covering dielectric is no longer deciding the thickness of the liquid layer, e.g., setting the distance, between the two devices. FIG. 10A is the MEMS heating device (104) of FIG. 8A, or equivalent thereof. FIG. 10B is a top view of a window device (102), complete with at least one spacer (150). FIG. 10C is a cross-section of the window device (102) of FIG. 10B positioned on the MEMS heating device of FIG. 10A, illustrating the "nestled" placement of the window device within the covering dielectric frame of the MEMS heating device.

Figure 11:
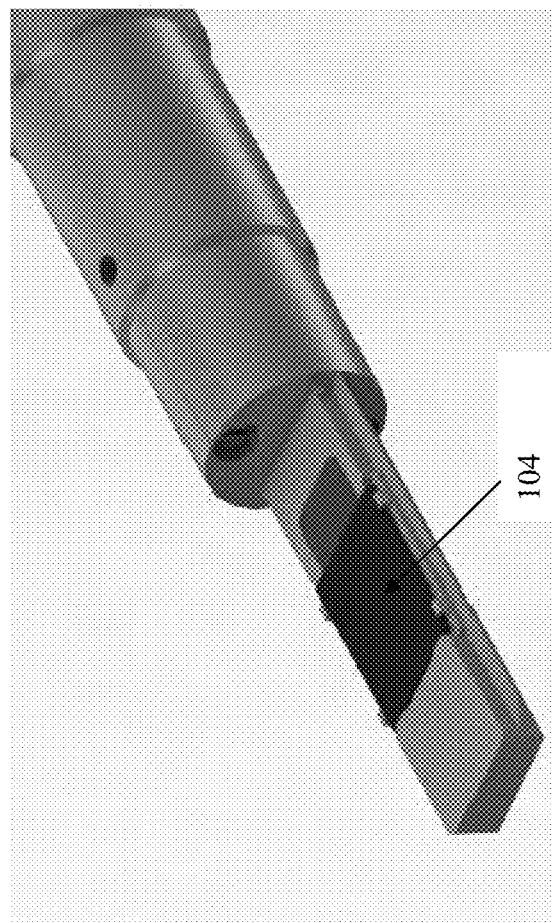
FIG. 11 illustrates an "open cell" sample tip.

Any of the MEMs heating devices described herein can be used in an "open cell" sample tip, for example, as shown in FIG. 11, wherein the device is open to the inside vacuum. The MEMs heating device of FIG. 9 is especially useful in the open cell sample tip.

In another alternative, any of the E-cells shown herein can include the MEMS heating device of FIGS. 9A-9C. An example of this would be an E-cell comprising the MEMS heating device with a small chip, i.e., a window device, whereby SEM imaging is carried out through the small chip window. This allows the user to heat liquids and/or gases while still performing SEM analysis. In this scenario, the sample would not be exposed to the SEM environment since it would be sealed between the two chips. It should be appreciated that the shape and arrangement of the heat source element in FIGS. 9A-9C is analogous to that shown in FIGS. 3A-3C but can be the shape and arrangement of that shown in FIGS. 1A-1C, 2A-2C, or any other shape and arrangement envisioned by those skilled in the art. Further, it should be appreciated that the covering dielectric in FIGS. 9A-9C is analogous to that shown in FIGS. 3A-3C but can be analogous to that shown in FIG. 1A-1C or 2A-2C.

Figure 12:
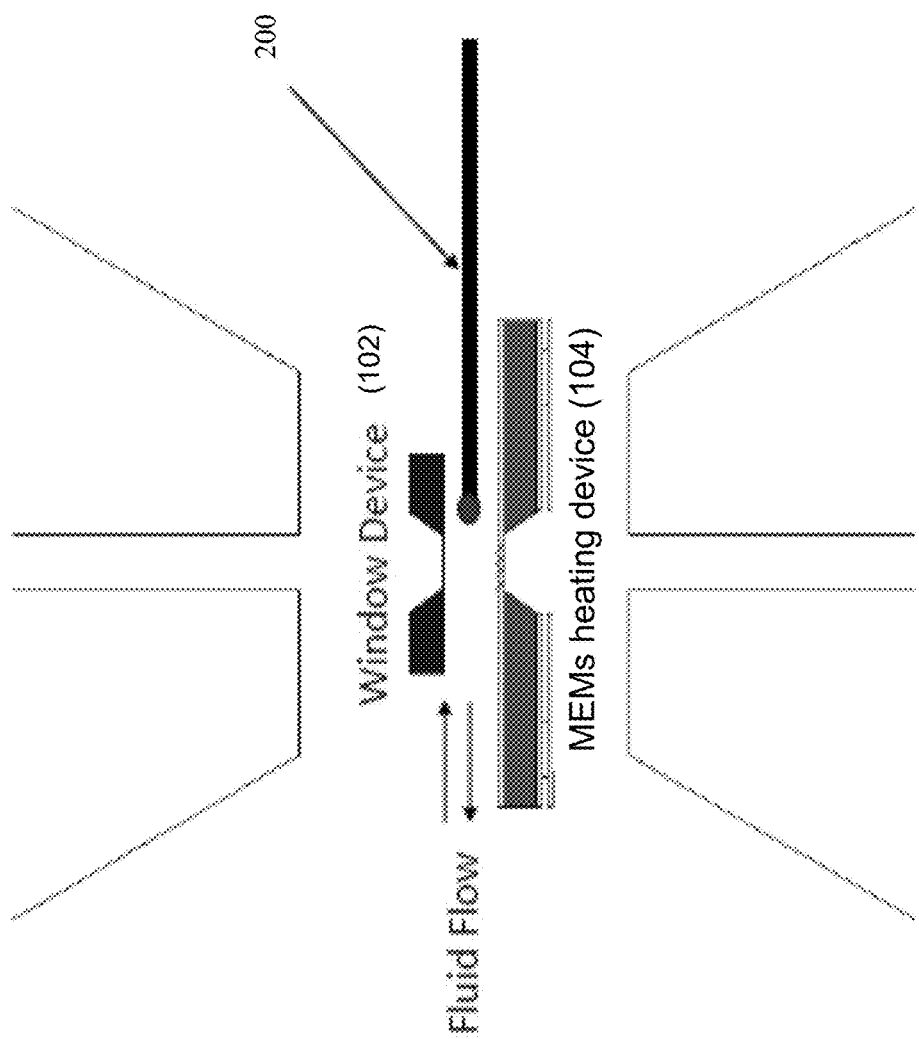
FIG. 12 illustrates a cross-sectional view of environmental cells (E-cell) formed using two devices where at least one external thermal sensor (200) is placed in proximity to the device to measure the other environmental conditions of the sample on the device.

FIG. 12 illustrates a cross-sectional view of environmental cells (E-cell) formed using two devices where at least one external thermal sensor (200) is placed in proximity to the device to measure the other environmental conditions of the sample on the device wherein the one or more environmental conditions is selected from a group consisting of liquid content and gas content. The thermal sensor can be a thermocouple or an RTD sensor.

Membrane or observation regions may contain additional elements that serve to provide an electrical source or sense element to the specimen or membrane region and/or to provide a temperature source or sense element to the specimen or membrane region.

As defined herein, "electrical sense element" means a component used to directly measure current or voltage on the device (e.g., temperature control device) and may be either frame or membrane, but typically membrane. Electrical contacts from the holder to the device can be used in conjunction with electrical sense elements. Electrical contacts are made by defining pad regions, and the pad regions are generally directly on the surface of the respective element itself and in a region over the frame. These pad regions are areas generally greater than about 100 microns by about 100 microns defined on the element either by 1) a patterned region of material where the pad material is different from the element material, or 2) a patterned region of the element where the pad region is comprised of the same material as the element material. The use of another material is preferred when a good and/or ohmic electrical contact cannot be achieved through a physical contact between the holder and the element material. If the element material is a metal such as tungsten, the pad region could simply be a large area within that element on the frame region. If the element material is a semiconductor or ceramic such as silicon carbide, a non-magnetic metal such as gold, tungsten, platinum, titanium, palladium or copper and non-magnetic alloys could be used. There may be multiple pads per element, and multiple elements per device. It is also possible to use a secondary circuit or set of electrodes that can source and measure independently of the heating element circuit, thus permitting for an electrochemistry or electro-thermal device that can make empirical electrical measurements of the sample or fluid independent of the heating circuit.

A method of imaging a specimen at multiple temperatures and/or while changing temperatures using an in situ microscopic device is also described herein, wherein the method comprises providing at least one MEMs heating device described herein, positioning the sample on the observation region, and controlling the temperature of the sample during imaging.

In another aspect, a microscopic device comprising the MEMs heating device described herein is disclosed, wherein said MEMs heating device is mounted in a manner which permits microscopic imaging of a sample on the device wherein the conductive elements are coupled to a source of electricity.

In still another aspect, a method of using a MEMS heating device to (i) measure dynamic thermal changes to the imaging environment, (ii) measure exo- or endo-thermal reactions between the sample and an introduced liquid or gas, (iii) measure exo- or endo thermal reactions caused by two mixing liquids in the reservoir, or (iv) electron beam effects during imaging, is described, said method comprising using the MEMS heating device described herein as a passive temperature sensor without actually heating the device. An example of an application where this method can be used would be calorimetry. The resistance of the metal coil (i.e., heat source element) on the MEMS heating device is effectively a temperature sensor since its resistance is a function of temperature, whereby a specific resistance correlates to a specific temperature. When a sample undergoes an endothermic or exothermic reaction at a specific temperature, for example, an exothermic reaction when certain polymers cross-link due to heating, the user would recognize this reaction occurred because of a sudden change in the resistance of the metal coil when you reach the cross-linking temperature. Alternatively, this method can be used to measure beam effects. When a sample is being hit with an electron beam, some of the electron energy is absorbed in the sample and can heat the sample up. One approach could be to heat the sample up without the electron beam on, note the resistance, then turn the beam on and measure the change in resistance at a fixed current. The additional heat measured would be attributed solely to beam effects.

While the invention has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

What is claimed is:

1. A device comprising: (a) at least one observation region, (b) a thermally conductive structural frame which supports and flanks the observation region, and (c) at least one heat source element supported by the thermally conductive structural frame, wherein the at least one heat source element flanks but does not contact the at least one observation region, and wherein the thermally conductive structural frame is heated by the at least one heat source element.

2. The device of claim 1, wherein the at least one observation region comprises at least one membrane, wherein the at least one membrane comprises one or more holes, comprises thinned dimples, or is a continuous membrane that is supported by the thermally conductive structural frame.

3. The device of claim 1, wherein the at least one heat source element is electrically insulated from the thermally conductive structural frame by a dielectric layer positioned therebetween.

4. The device of claim 1, wherein the at least one heat source element comprises a covering dielectric to electrically insulate the at least one heat source element from any one or more environmental conditions selected from the group consisting of liquid content, gas content and external supports.

5. The device of claim 1, wherein the at least one heat source element is electrically insulated from the thermally conductive structural frame by a dielectric layer positioned therebetween and wherein the at least one heat source element comprises a covering dielectric to electrically insulate the heat source element(s) from any one or more environmental conditions selected from the group consisting of liquid content, gas content or external supports.

6. The device of claim 1, where the at least one heat source element comprises at least one material selected from the group consisting of tungsten, platinum, tantalum, rhenium, molybdenum, titanium, nichrome, kanthal, cupronickel, polysilicon, silicide, silicon carbide, titanium carbide, molybdenum disilicide, molybdenum carbide, tungsten carbide, tungsten nitride, tantalum nitride, boron nitride, FeCrAl, NiCr, titanium silicide, tantalum silicide, cobalt silicide, titanium nitride, and aluminum nitride.

7. The device of claim 1, wherein the thermally conductive structural frame heats the at least one observation region by thermal energy.

8. The device of claim 1, further comprising at least two exposed conductive contacts that can be connected to a source of electricity.

9. The device of any one of claims 1-8, wherein the at least one heat source element is positioned on the same side of the thermally conductive structural frame as the at least one observation region.

10. The device of any one of claims 1-8, wherein the at least one heat source element is positioned on an opposite side of the thermally conductive structural frame as the at least one observation region.

11. The device of claim 1, wherein the thickness of at least one observation region is in a range from about 0.00001 μm to about 1 μm.

12. The device of claim 4, wherein the covering dielectric covers the entire device except over the at least one observation region.

13. The device of claim 4, wherein the covering dielectric covers just the at least one heat source element, wherein the at least one heat source element is positioned around the perimeter of the device.

14. The device of claim 5, wherein:
the dielectric layer comprises the same material as the covering dielectric;
the dielectric layer comprises a different material than the covering dielectric; or
the dielectric layer comprises the same material as the covering dielectric, and the dielectric layer and the covering dielectric have at least one of a different porosity and a different density.

15. A microscope device comprising the device of claim 1 mounted in a manner which permits microscopic imaging of a sample on the device wherein the at least one heat source element is coupled to a source of electricity.

16. A method of imaging a sample at one or more temperatures using an in situ microscope device, the method comprising providing the device of claim 15, positioning the sample at the observation region, and controlling heating by the at least one heat source element during imaging.

17. An environmental cell comprising the device of claim 1 configured to permit control of: (a) heating of a sample on the observation region of the device through conduction from the thermally conductive structural frame; and (b) heating of one or more environmental conditions of the sample on the observation region of the device, wherein at least one of the one or more environmental conditions is selected from the group consisting of liquid content and gas content.

18. The environmental cell of claim 17, further comprising at least one of a MEMS heating device and a window device.

19. The environmental cell of claim 17, comprising at least one external thermal sensor to measure the at least one of the one or more environmental conditions.

20. The environmental cell of claim 19, wherein the at least one external thermal sensor is a thermocouple or RTD sensor placed in proximity to the device.

* * * * *